(12) United States Patent
Lin et al.

(10) Patent No.: US 7,213,540 B2
(45) Date of Patent: May 8, 2007

(54) STEAM RECOMPRESSION IN CARBOXYLIC ACID PROCESSES

(75) Inventors: Robert Lin, Kingsport, TN (US); Steven Paul Bellner, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 465 days.

(21) Appl. No.: 10/772,819

(22) Filed: Feb. 5, 2004

(65) Prior Publication Data
US 2005/0176992 A1    Aug. 11, 2005

(51) Int. Cl.
*F22D 1/40* (2006.01)
*C07C 51/16* (2006.01)

(52) U.S. Cl. .................... 122/422; 562/407
(58) Field of Classification Search ............ 562/414, 562/404, 409, 412, 413, 407; 122/406.1, 122/422
See application file for complete search history.

(56) References Cited

U.S. PATENT DOCUMENTS

| | | | |
|---|---|---|---|
| 3,970,696 | A | 7/1976 | Shigeyasu et al. |
| 3,996,271 | A | 12/1976 | Yokota et al. |
| 4,158,738 | A | 6/1979 | Scott et al. |
| 4,356,319 | A | 10/1982 | Roffia et al. |
| 4,939,297 | A | 7/1990 | Browder et al. |
| 5,463,113 | A | 10/1995 | Yamamoto et al. |
| 5,510,521 | A | 4/1996 | McGeehee et al. |
| 5,567,842 | A | 10/1996 | Izumisawa et al. |
| 5,612,007 | A | 3/1997 | Abrams |
| 5,723,656 | A | 3/1998 | Abrams |
| 5,959,140 | A | 9/1999 | Okoshi |
| 5,961,942 | A | 10/1999 | Turner et al. |

(Continued)

FOREIGN PATENT DOCUMENTS

EP    0 734 372 B1    5/2000

(Continued)

OTHER PUBLICATIONS

Hung, T.C., Shai, T.Y. and Wang, S.K., *A Review of Organic Rankine Cycles for the Recovery of Low-Grade Waste Heat*, Energy, 1997, pp. 661-667, vol. 22, No. 7, Elsevier Science Ltd., Great Britain.

(Continued)

*Primary Examiner*—Taylor Victor Oh
(74) *Attorney, Agent, or Firm*—Steven A. Owen; Bernard J. Graves, Jr.

(57) ABSTRACT

Disclosed is a method for the re-compression of process generated steam to create a higher pressure steam that is useful as a heating medium in other parts of a carboxylic acid production process or, in general utilized in another process. The invention comprises the following basic steps: (a) recovering thermal energy from at least a portion of the high temperature process stream resulting from an aromatic carboxylic acid production process in a first heat transfer zone to produce a low pressure stream; (b) subjecting the low pressure steam to a compression zone to generate an intermediate pressure steam; (c) utilizing the intermediate pressure steam as a heating medium, specifically within other parts of the carboxylic acid process or generally in another process thereby generating steam condensate; and (d) optionally, recycling all or part of the steam condensate to the second heat transfer zone for low pressure steam generation.

39 Claims, 3 Drawing Sheets

U.S. PATENT DOCUMENTS

| | | |
|---|---|---|
| 6,143,926 A | 11/2000 | Parten |
| 6,504,051 B1 | 1/2003 | Miller, Jr. et al. |
| 6,831,195 B2 | 12/2004 | Nishimura et al. |

FOREIGN PATENT DOCUMENTS

| | | |
|---|---|---|
| GB | 1 373 230 | 11/1974 |
| JP | 5-213816 A | 8/1993 |
| JP | 11-349523 A | 12/1999 |
| WO | WO02/06201 A1 * | 1/2002 |
| WO | WO 02/063141 A1 | 8/2002 |

OTHER PUBLICATIONS

Hung, T.C., *Waste Heat Recovery of Organic Rankine Cycle Using Dry Fluids*, Energy, 2001, pp. 539-553, Elsevier Science Ltd.

Ibrahim, O.M. Klein, S.A., *Absorption Power Cycles*, Energy, 1996, pp. 21-27, vol. 21, No. 1, Elsevier Science Ltd. Great Britain.

Ryans, J.L. and Roper, D.L., *Steam Jets Ejectors*, Process Vacuum System Design and Operation, 1986, pp. 229-260, Ch. 9, McGraw Hill.

Copending U.S. Appl. No. 10/617,878, filed Jul. 10, 2003.

* cited by examiner

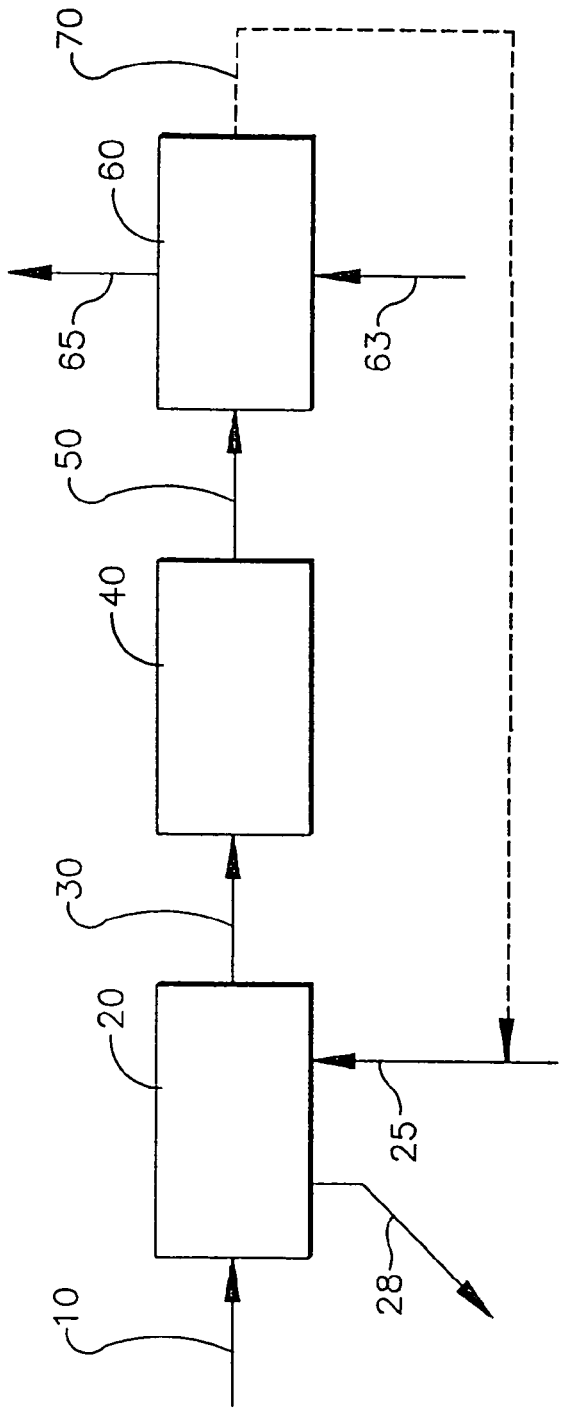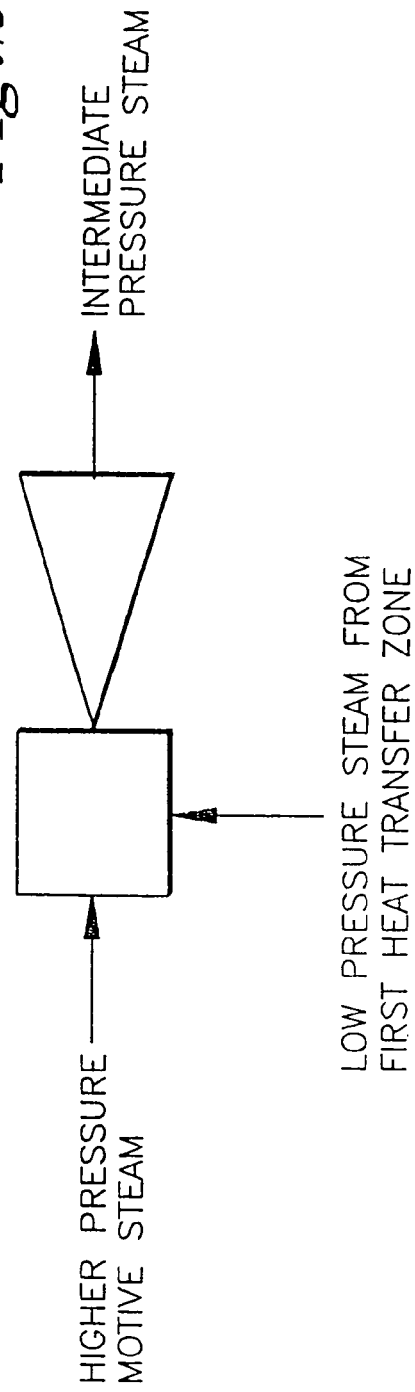

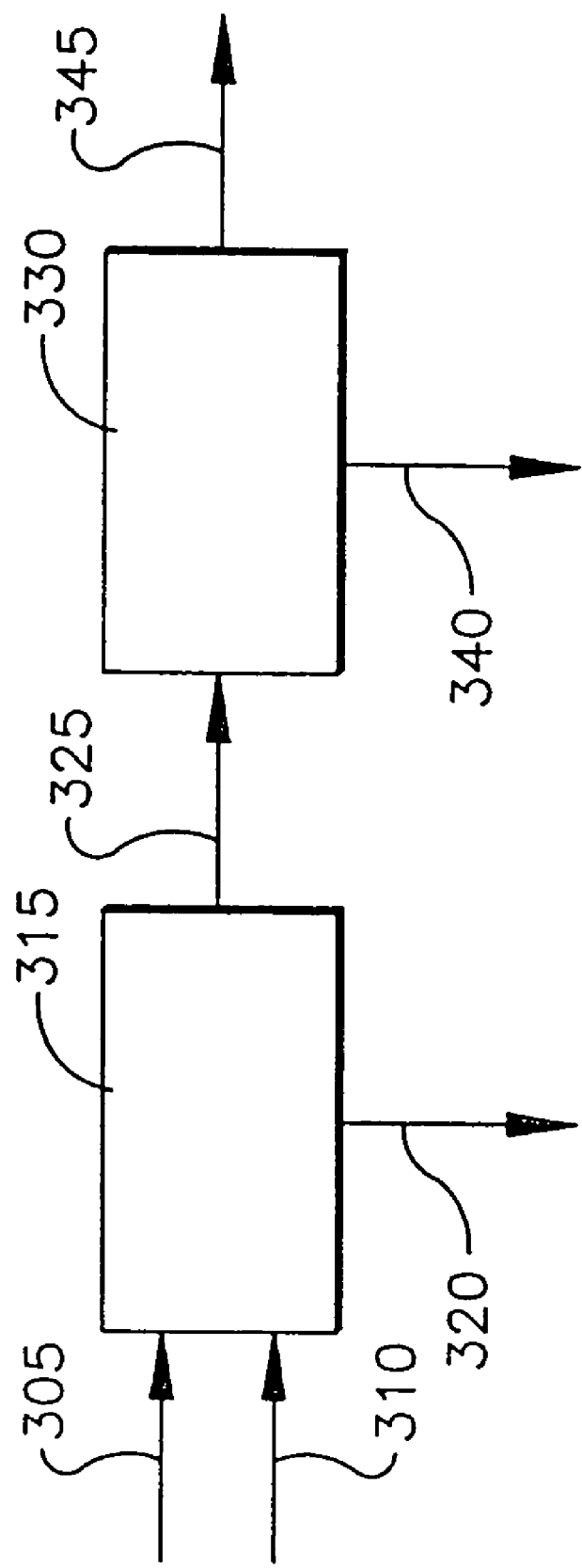

STEAM RECOMPRESSION IN CARBOXYLIC ACID PROCESSES

FIELD OF INVENTION

This invention is related to the efficient energy integration within an aromatic carboxylic acid production facility by utilizing the reaction exotherm as a source of energy for a steam heating medium to produce low pressure steam and then subjecting the low pressure steam to a compression zone to form an intermediate pressure steam.

BACKGROUND OF THE INVENTION

Aromatic carboxylic acids, such as terephthalic acid, isophthalic acid, and napthlene dicarboxylic acid are useful chemical compounds and are raw materials in the production of polyesters and copolyesters. In the instance of terephthalic acid, a single manufacturing facility can produce greater than 100,000 metric tons per annum as feedstock for a polyethylene terephthalate (PET) facility.

Terephthalic acid (TPA) can be produced by the high pressure, exothermic oxidation of a suitable aromatic feedstock such as para-xylene in a solvent such as acetic acid, water, or mixtures thereof. Typically, these oxidations are carried out in a liquid phase using air or alternate sources of molecular oxygen in the presence of metal catalyst(s) or promoter compound(s). Methods for oxidizing para-xylene and other aromatic compounds such as m-xylene and dimethylnapthlene are well known in the art.

In addition to oxidation, many industrial TPA processes also incorporate a hydrotreating (hydrogenation) process to produce a so-called purified terephthalic acid or PTA. Typically, these processes are conducted using a water solvent. These hydrogenation processes are also well known in the art.

TPA processes give rise to high temperature material streams. These streams are derived from both the heating needs within the process and heat removal needs. Typical would be to provide some sort of heat input which would result in the boiling or evaporation of a solvent. Energy could then be recovered via condensation of the solvent.

As the art has progressed, a significant body of literature has been developed to address the problem of efficient energy recovery within the TPA process. In general, these schemes usually involve the recovery of useful work/electricity via the use of a turbine and/or the recovery of heat energy via the use of steam generation. Both of these general schemes have certain drawbacks and limitations.

In the case of recovery of work/electricity via the use of a turbine, there are significant technical and economic problems. In the case of steam generation, the technical problems of physically producing steam are relatively insignificant. However, the limitations are generally associated with the usefulness of the steam generated. Specifically, the steam generated from TPA processes generally is at too low a temperature and/or pressure to be useful as a heating medium in general. And specifically within the remainder of the process.

Although, by themselves mechanical energy recovery via a turbine and heat energy recovery via steam generation are not necessarily novel, the objective of this invention is to describe a method of heat energy recovery involving the generation of steam followed by processing of the generated steam into a more useful form.

SUMMARY OF THE INVENTION

Disclosed are various configurations for producing steam in carboxylic acid production processes. Although steam generation within terephthalic acid production processes in itself is well known, this invention discloses a method for the re-compression of process generated low pressure steam to create an intermediate pressure steam that is useful as a heating medium, specifically in other parts of the terephthalic acid production process or generally utilized in another process. The invention comprises the following basic steps:

1. Recovering thermal energy in a first heat transfer zone from a high temperature process stream and then using the thermal energy to generate a low pressure steam; wherein the high temperature material stream is a result of an aromatic carboxylic acid production process;
2. Subjecting the low pressure steam to a compression zone to generate an intermediate pressure steam;
3. Utilizing the intermediate pressure steam in a second heat transfer zone as a heating media, specifically within other parts of the terephthalic acid (or other aromatic carboxylic acid) process or generally utilized in another process thereby generating steam condensate; and
4. Optionally, recycling all or part of the steam condensate to the first heat transfer zone for low pressure steam generation.

It is an object of this invention to provide a process to produce an intermediate pressure steam from a high temperature process stream.

It is another object of this invention to provide a process to recover thermal energy from a high temperature process stream wherein the carboxylic acid vapor stream comprising primarily any acetic acid or any solvent in a carboxylic acid production process, water, and mixture thereof.

It is another object of this invention to provide a process for efficient energy integration within a carboxylic acid production facility by utilizing the reaction exotherm from at least one oxidation reaction directly or indirectly as a source of energy for a steam heating medium to produce low pressure steam and then subjecting the low pressure steam to a compression zone to form an intermediate pressure steam.

It is another object of this invention to provide a process for efficient energy integration within the terephthalic acid production facility by utilizing the reaction exotherm from at least one oxidation reaction directly or indirectly as a source of energy for a steam heating medium to produce low pressure steam and then subjecting the low pressure steam to a compression zone to form an intermediate pressure steam.

In one embodiment of the invention, a process to produce an intermediate pressure steam from a high temperature process stream is provided. The process comprises:

(a) recovering thermal energy from at least a portion of the high temperature process stream in a first heat transfer zone to produce a low pressure steam; and (b) compressing the low pressure steam in a compression zone to produce an intermediate pressure steam.

In another embodiment of the invention, a process to recover thermal energy from a high temperature process stream is provided. The process comprises:

(a) recovering thermal energy from at least a portion of the high temperature process stream in a first heat transfer zone to produce a low pressure steam;

(b) compressing the low pressure steam in a compression zone to produce an intermediate pressure steam;

(c) recovering thermal energy from at least a portion of the intermediate pressure steam in a second heat transfer zone to produce steam condensate; and (d) optionally recycling at least a portion of the steam condensate to the first heat exchange zone.

In another embodiment of this invention, a process to recover thermal energy from a high temperature process stream is provided. The process comprises:

(a) recovering thermal energy from at least a portion of the high temperature process stream in a first heat transfer zone to produce a low pressure steam;

(b) compressing the low pressure steam in a compression zone to produce a intermediate pressure steam; wherein the compression zone comprises at least one steam ejector;

(c) recovering thermal energy from at least a portion of the intermediate pressure steam in a second heat transfer zone to produce steam condensate; and (d) optionally recycling at least a portion of the steam condensate to the heat exchange zone.

In another embodiment of this invention, a process to recover thermal energy from a high temperature process stream is provided. The process comprises:

(a) recovering thermal energy from at least a portion of the high temperature process stream in a first heat transfer zone to produce a low pressure steam;

(b) compressing the low pressure steam in a compression zone to produce a intermediate pressure steam; wherein the compression zone comprises at least one compressor;

(c) removing at least a portion of superheat resulting from compression from said intermediate pressure steam;

(d) recovering thermal energy from at least a portion of the intermediate pressure steam in a second heat transfer zone to produce steam condensate; and (e) optionally recycling at least a portion of the steam condensate to the heat exchange zone.

In another embodiment of this invention, a process to recover thermal energy from a high temperature process stream is provided. The process comprises:

(a) oxidizing an aromatic feedstock with a reaction mixture in a reaction zone to form an aromatic carboxylic acid-rich stream and a gaseous mixture;

(b) removing in a separation zone a substantial portion of a solvent from the gaseous mixture to form the high temperature process stream and a solvent rich stream; and (c) recovering thermal energy from at least a portion of the high temperature process stream in a first heat transfer zone to produce a low pressure steam;

(d) compressing the low pressure steam in a compression zone to produce an intermediate pressure steam;

(e) recovering thermal energy from at least a portion of the intermediate pressure steam in a second heat transfer zone to produce steam condensate; and (f) optionally recycling at least a portion of the steam condensate to the heat exchange zone.

These objects, and other objects, will become more apparent to others with ordinary skill in the art after reading this disclosure.

BRIEF DESCRIPTION OF THE DRAWINGS

FIG. 1 illustrates one embodiment of this invention. A process is provided to recover thermal energy from a high temperature process stream to produce a low pressure steam and then subjecting the low pressure steam to a compression zone to form an intermediate pressure steam.

FIG. 2 illustrates steam compression using a steam ejector.

FIG. 4 illustrates one of many examples of a process for producing a high temperature process stream.

DETAILED DESCRIPTION OF THE INVENTION

Figure 3:
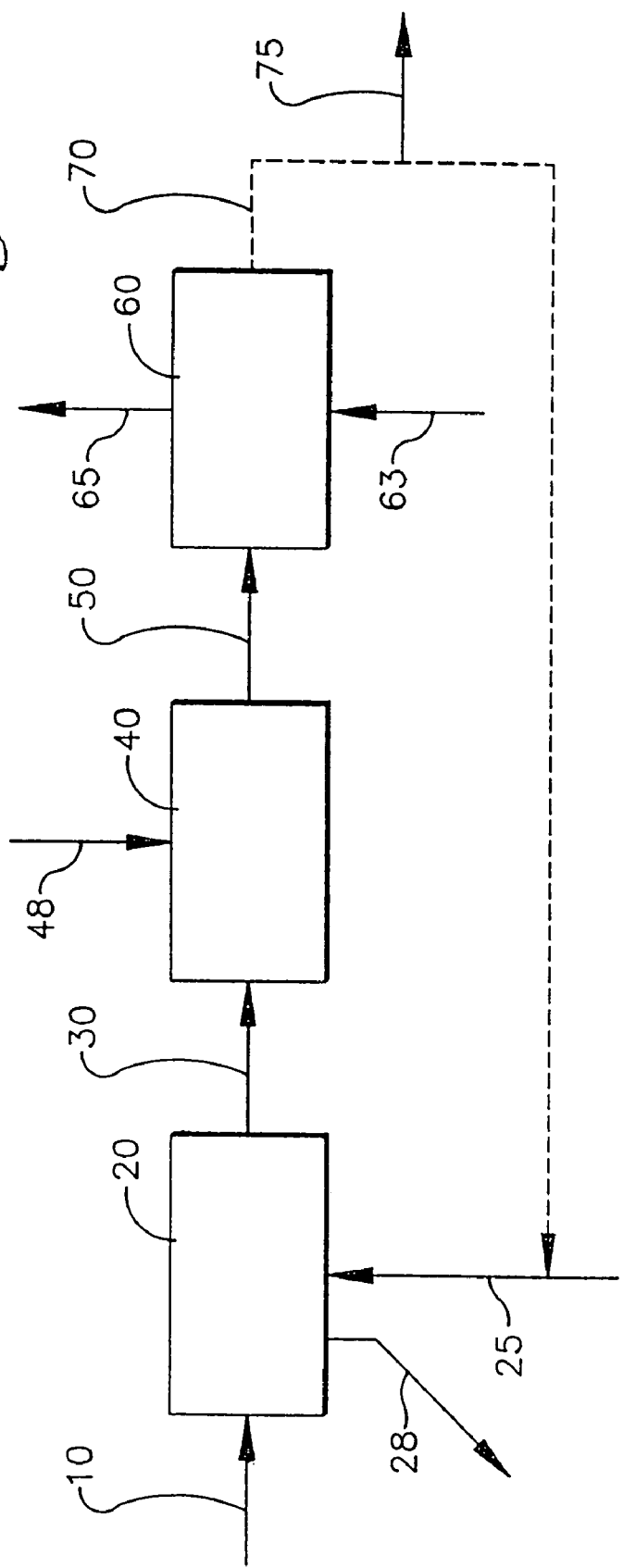
FIG. 3 illustrates one embodiment of this invention. A process is provided to recover thermal energy from a high temperature process stream to produce a low pressure steam and then subjecting the low pressure steam to a compression zone to form an intermediate pressure steam; wherein the compression zone comprises at least one steam ejector.

Various embodiments are disclosed for producing steam in carboxylic acid production processes. Carboxylic acids include, but are not limited to, aromatic carboxylic acids produced via controlled oxidation of an organic substrate. Such aromatic carboxylic acids include compounds with at least one carboxylic acid group attached to a carbon atom that is part of an aromatic ring, preferably having at least 6 carbon atoms, even more preferably having only carbon atoms. Suitable examples of such aromatic rings include, but are not limited to, benzene, biphenyl, terphenyl, naphthalene, and other carbon-based fused aromatic rings. Examples of suitable carboxylic acids include, but are not limited to, terephthalic acid, benzoic acid, p-toluic acid, isophthalic acid, trimellitic acid, naphthalene dicarboxylic acid, and 2,5-diphenyl-terephthalic acid.

In one embodiment of this invention, a process to recover thermal energy from a high temperature process stream 10 is provided. The process comprises:

Step (a) recovering thermal energy from at least a portion of the high temperature process stream 10 in a first heat transfer zone 20 to produce a low pressure steam 30. In an embodiment of the invention, the high temperature process stream 10 is partially or fully condensed in a first heat transfer zone 20 which comprises at least one heat transfer device. The heat transfer can be accomplished by any heat transfer devices known in the art such that heat is transferred without combining the high temperature process stream 10 and the water/steam condensate stream 25. For example, the heat transfer device could be a shell and tube heat exchanger. Heat is transferred to water/steam condensate 25 in the first heat transfer zone 20 allowing the water to vaporize to produce a low pressure steam 30. The condensed or partially condensed high temperature process stream exit the first heat transfer zone 20 via conduit 28. Although steam generation via this method is well-known in the art, the usefulness of the steam generated is limited by the choice of the high temperature process stream 10. In general, it is most desirable to use a high temperature process stream 10 with the highest temperature available. This is because the pressure and temperature of the steam generated is an important factor in the usefulness and efficiency for the purpose of mechanical energy generation and for use as a heating medium.

In general, there are no limitations on the condition or origin of the high temperature process stream 10 in this invention with the exception that the high temperature process stream 10 is at a sufficient inlet temperature to the first heat transfer zone 20 to produce a low pressure steam 30 at or above atmospheric pressure. The high temperature process stream 10 is at a temperature sufficient to produce steam at a temperature about 100° C. to about 140° C. Both the low pressure steam 30 and intermediate pressure steam 50 disclosed in this invention is at saturation or superheated temperatures. Preferably, the high temperature process stream 10 is at a temperature greater than 100° C.

The high temperature process stream 10 can be any high temperature stream that exists in an aromatic carboxylic acid production process. The high temperature process stream 10 does not necessarily comprise an aromatic carboxylic acid.

Examples of suitable high temperature process streams 10 include but are not limited to vapor from an oxidation reactor or high pressure distillation column described in E.P Patent 0734372, herein incorporated by reference, vapor generated by an oxidation reactor or water removal column described in U.S. Pat. Nos. 5,501,521 and 6,504,051, herein incorporated by reference, vapor generated by the crude TPA crystallizer or purified TPA crystallizer described in U.S. Pat. No. 5,723,656, herein incorporated by reference, or vapor generated by purified TPA crystallizers described in U.S. Pat. No. 5,567,842, herein incorporated by reference.

The high temperature process stream 10 can be produced by any aromatic carboxylic acid production process known in the art. For example as shown in FIG. 4, in one embodiment of the invention a process for producing the carboxylic acid vapor stream 10 comprises:

Step (i) comprises oxidizing an aromatic feedstock 305 with a reaction mixture 310 in a reaction zone 315 to form an aromatic carboxylic acid-rich stream 320 and a gaseous mixture 325.

The reaction mixture 310 comprises water, a solvent, a metal oxidation catalyst and a source of molecular oxygen. The reaction zone 315 comprises at least one oxidation reactor. The oxidizing is completed under reaction conditions which produce the aromatic carboxylic acid-rich stream 320 and the gaseous mixture 325. Typically, the aromatic carboxylic acid-rich stream 320 is a crude terephthalic acid slurry.

Crude terephthalic acid is conventionally made via the liquid phase air oxidation of paraxylene in the presence of a metal oxidation catalyst. Suitable catalysts include, but are not limited to, cobalt, manganese and bromine compounds, which are soluble in the selected solvent. Suitable solvents include, but are not limited to, aliphatic mono-carboxylic acids, preferably containing 2 to 6 carbon atoms, or benzoic acid and mixtures thereof and mixtures of these compounds with water. Preferably the solvent is acetic acid mixed with water, in a ratio of about 5:1 to about 25:1, preferably between about 10:1 and about 15:1. However, it should be appreciated that other suitable solvents, such as those disclosed herein, may also be utilized. Conduit 325 contains a gaseous mixture which comprises vaporized solvent, gaseous by-products, nitrogen and unreacted oxygen generated as a result of an exothermic liquid phase oxidation reaction of an aromatic to an aromatic carboxylic acid. Patents disclosing the production of terephthalic acid such as U.S. Pat. Nos. 4,158,738 and 3,996,271 are hereby incorporated by reference.

Step (ii) comprises removing in a separation zone 330 a substantial portion of the solvent from the gaseous mixture 325 to form the high temperature process stream 345 and a solvent rich stream 340.

The high temperature process stream 345 comprises water, gaseous by-products, and small amounts of solvent. When the solvent is a low molecular weight carboxylic acid solvent, the ratio of water to low molecular weight carboxylic acid solvent is in the range of about 80:20 to about 99.99:0.01 by mass. The gaseous by-products comprise oxygen, oxidation by-products, such as, carbon monoxide and carbon dioxide, and in the instance when air is used as a source of molecular oxygen, nitrogen. At least a portion of the high temperature process stream or all of the high temperature process stream is sent on to a first heat transfer zone via conduit 345. The portion of the high temperature process stream 345 that is sent to the first heat transfer zone 20 is shown on FIG. 1 via conduit 10.

Typically, the temperature and pressure conditions of the high temperature process stream 345 are in the range of about 130° C. to about 260° C. and about 3.5 to about 40 barg. Preferably, the temperature and pressure conditions of the high temperature process stream 345 are in the range of about 90° C. to about 200° C. and about 4 barg to about 15 barg. Most preferably, the temperature and pressure conditions of the high temperature process stream 345 are in the range of about 130° C. to about 180° C. and about 4 barg to about 10 barg.

The gaseous mixture in conduit 325 is directed to the separation zone 330. Typically, the separation zone 330 comprises a high pressure distillation column having between about 20 and about 50 theoretical stages and a condenser or plurality of condensers. In the separation zone 330, the solvent rich stream is recovered via conduit 340. The purpose of the separation zone 330 is to perform a separation wherein at least a portion of the solvent is recovered and excess water is removed. In general, for the purposes of optimized energy recovery, there should be minimal pressure reduction between the contents of conduit 325 and conduit 345 since this represents a loss of potentially recoverable energy. Therefore, the separation zone 330 should operate at temperature and pressure conditions at or near that of the gaseous mixture from conduit 325. At least a portion or all of the high temperature process stream 345 is sent to a first heat transfer zone, and the rest of the high temperature process stream can be utilitized elsewhere within the process for producing the aromatic carboxylic acid.

Step (b) comprises compressing the low pressure steam 30 in a compression zone 40 to produce an intermediate pressure steam 50. This step refers to subjecting the low pressure steam 30 to a compression process to generate the intermediate pressure steam 50. In one embodiment of the invention the intermediate pressure steam can be at about 50 psig to about 260 psig. Another range can be at about 50 psig to about 100 psig. The compression zone 40 comprises at least one compression device. For example, compression devices can include, but are not limited to a centrifugal compressor, a positive displacement compressor, and or a steam ejector. The compression device(s) can operate at a temperature and pressure sufficient to produce the intermediate pressure steam. It is desirable to produce steam close to its saturation temperature, owing to the excellent heat transfer properties of saturated steam. If there is too much superheat in the steam then the heat transfer in the second heat transfer zone will be inefficient. Superheat added by compression device can be removed or desuperheated before the intermediate pressure steam is sent to the second heat transfer zone. Desuperheating is also known as "superheat attemporation" or steam conditioning. For example, almost all types of desuperheaters operate by introducing a spray of liquid water into the superheated steam stream. This spray vaporizes, thus consuming the superheat to provide the heat of vaporization. Typically, the only difference between the types of desuperheaters is the mechanism in which the water is atomized and mixed with the steam. An example of a desuperheating device would be a probe-type desuperheater that automatically admits cooling water into the stream in response to a pneumatic control signal. The water enters through a spray bar with atomizing nozzles. Typically the spray bar is perpendicular to the flow of the steam. Another type of device is an annular desuperheater. Water is introduced into an annular body in the steam pipe which results in intensive turbulence that assists in the atomization of the water. A third common device is the Venturi desuperheater. This device uses the velocity of the steam through a venturi to assist in the final atomization of the water. The water is introduced in the throat of the venture. Methods for removing superheat are well known in the art.

Table 1 below provides a summary of compression devices and conditions. The compression ratios are calculated using absolute pressure and represent preferred ranges only.

TABLE 1

Methods of Steam Compression to Higher Pressure

| Compression Device | Inlet Conditions | Compression Ratio ($P_{outlet}/P_{inlet}$) | Outlet Conditions |
|---|---|---|---|
| Centrifugal Compressor | Saturated Steam or Superheated Steam @ P > 14 psia | 1.5 to 5 | Saturated or superheated steam at P > 29 psia |
| Positive Displacement Compressor | Saturated Steam or Superheated heated @ P > 14 psia | 1.5 to 10 | Saturated or superheated steam at P > 29 psia |
| Steam Ejector | Saturated Steam or Superheated heated @ P > 14 psia and high pressure motive steam | 1.2 to 3 | Saturated steam at P > 29 psia |

In most cases, a simple compression device can be utilized for the direct compression of low pressure steam to an intermediate pressure. However, in the case of a steam ejector, high pressure motive fluid (i.e. high pressure steam) can be used to "mix" high and low pressure steam 30 to generate an intermediate pressure steam 50. A simplified schematic is shown in FIG. 2. FIG. 3 shows and embodiment of the invention utilizing the steam ejector. FIG. 3 shares all the same process streams as FIG. 1 with the exception of conduit 48 and 75 which are the condensed or partially condensed high pressure steam 48 and the condensate 75 that is not optionally recycled back to the first heat transfer zone 20. The high pressure steam 48 can either be at saturated or superheated temperature. Equipment sizing and motive steam requirements can be calculated by conventional methods known in the art. Examples of such methods can be found in Ryans and Roper, "Process Vacuum System Design and Operation", McGraw-Hill, 1986.

Step (c) comprises recovering thermal energy from at least a portion of the intermediate pressure steam 50 in a second heat transfer zone 60 to produce steam condensate 70. This step refers to utilizing the intermediate pressure steam 50 as a heating media within other parts of the process thereby generating steam condensate 70. In general, there are no limitations for the use of intermediate pressure steam 50 within the TPA process or any carboxylic acid process known in the art. However, the preferred use for the intermediate pressure steam 50 as a heating medium is for the purpose of evaporation of acetic acid/water mixtures. Conduit 63 and 65 represent a process stream in an aromatic carboxylic acid production process that recovers energy from the intermediate pressure steam 50. Heat is transferred without combining stream 63 and 50. Examples of possible intermediate pressure steam 50 uses include, but not limited to, an evaporator as described is U.S. Pat. No. 4,939,297 herein incorporated by reference, a distillation column reboiler(s) used in conjunction with the process described in U.S. Pat. No. 4,939,297, an evaporator as described in U.S. Pat. No. 4,356,319 herein incorporated by reference, a preheater as described in U.S. Pat. No. 5,961,942 or EP 0734372 herein incorporated by reference, an acetic acid/water separation column reboiler as describe in U.S. Pat. No. 6,143,926 and U.S. Pat. No. 5,959,140 herein incorporated by reference. These examples are intended to be a non-inclusive example list.

In addition to the examples provided above, the steam can also be utilized for non-process specific purposes. Examples include, but are not limited to heat tracing, generation of refrigeration, an energy source for heating, ventilation, and air conditioning (HVAC) purposes, and export of intermediate pressure steam to an external user or customer, or process.

Step (d) comprises optionally recycling at least a portion of the steam condensate 70 to the first heat transfer zone 20. This step refers to recycling of all or part of the steam condensate 70 to the first heat transfer zone 20 to generate low pressure steam 30. In general, there are no limitations on the condition of the steam condensate 70 with the exception that it is of sufficient pressure to supply to the heat transfer device that is utilized in the first heat transfer zone 20. For example, in nearly all instances, a pump or similar device can be utilized to provide sufficient pressure.

In the embodiment where the compression zone 40 comprises at least one steam ejector is shown in FIG. 3. High pressure steam is sent into the steam ejector via conduit 48. In addition, the excess condensate is taken off via conduit 75.

We claim:

1. A process to produce an intermediate pressure steam from a high temperature process stream resulting from an aromatic carboxylic acid production process, said process comprising:
   (a) recovering thermal energy from at least a portion of said high temperature process stream in a first heat transfer zone to produce a low pressure steam; and
   (b) compressing said low pressure steam in a compression zone to produce said intermediate pressure steam; wherein said intermediate pressure steam has a pressure in the range from about 50 psig to about 260 psig.

2. A process according to claim 1 wherein said low pressure steam has a pressure from about 0 psig to about 40 psig.

3. A process according to claim 1, or 2 wherein said compression zone comprises at least one compression device selected from the group consisting of a centrifugal compressor, a positive displacement compressor, and a steam ejector.

4. A process according to claim 3 wherein said intermediate pressure steam is superheated and wherein at least a portion of the superheat is removed from said intermediate pressure steam.

5. A process according to claim 1, or 2 wherein said compression zone comprises at least one steam ejector.

6. A process according to claim 5 wherein said steam ejector has a compression ratio of about 1.2 to about 2.0.

7. A process according to claim 6 wherein said high temperature process stream is at a temperature of greater than 100° C.

8. A process according to claim 1 wherein said high temperature process stream is produced in a carboxylic acid production process and wherein the high temperature process stream is generated from an oxidation reactor, high pressure distillation column, vapor generated by an oxidation reactor, a water removal column, vapor generated by the crude TPA crystallizer, purified TPA crystallizer described, or vapor generated by purified TPA crystallizers.

9. A process according to claim 1 wherein said high temperature process stream is produced in a terephthalic acid production process.

10. A process to recover thermal energy from a high temperature process stream resulting from an aromatic carboxylic acid production process, said process comprising:
   (a) recovering thermal energy from at least a portion of said high temperature process stream in a first heat transfer zone to produce a low pressure steam;
   (b) compressing said low pressure steam in a compression zone to produce an intermediate pressure steam; wherein said intermediate pressure steam has a nressure in the range from about 50 psig to about 260 psig;
   (c) recovering thermal energy from at least a portion of said intermediate pressure steam in a second heat transfer zone to produce steam condensate; and
   (d) optionally, recycling at least a portion of said steam condensate to said first heat transfer zone.

11. A process according to claim 10 wherein said low pressure steam has a pressure from about 0 psig to about 40 psig.

12. A process according to claim 10, or 11 wherein said compression zone comprises at least one compression device selected from the group consisting of a centrifugal compressor, a positive displacement compressor, and a steam ejector.

13. A process according to claim 12 wherein said intermediate pressure steam is superheated and wherein at least a portion of the superheat is removed from said intermediate pressure steam.

14. A process according to claim 10, or 11 wherein said compression zone comprises at least one steam ejector.

15. A process according to claim 14 wherein said steam ejector has a compression ratio of about 1.2 to about 2.0.

16. A process according to claim 15 wherein said high temperature process stream is at a temperature of greater than 100° C.

17. A process according to claim 15 wherein said high temperature process stream is produced in a carboxylic acid production process and wherein the high temperature process stream is generated from an oxidation reactor, high pressure distillation column, vapor generated by an oxidation reactor, a water removal column, vapor generated by the crude TPA crystallizer, purified TPA crystallizer described, or vapor generated by purified TPA crystallizers.

18. A process according to claim 15 wherein said high temperature process stream is produced in a terephthalic acid production process.

19. A process to recover thermal energy from a high temperature process stream resulting from an aromatic carboxylic acid production process, said process comprising:
   (a) recovering thermal energy from at least a portion of said high temperature process stream in a first heat transfer zone to produce a low pressure steam;
   (b) compressing said low pressure steam in a compression zone to produce a intermediate pressure steam; wherein said compression zone comprises at least one steam ejector; wherein said intermediate pressure steam has a pressure in the range from about 50 psig to about 260 psig;
   (c) recovering thermal energy from at least a portion of said intermediate pressure steam in a second heat transfer zone to produce steam condensate; and
   (d) optionally recycling at least a portion of said steam condensate to said first heat transfer zone.

20. A process according to claim 19 wherein said low pressure steam has a pressure from about 0 psig to about 40 psig.

21. A process according to claim 19 wherein said steam ejector has a compression ratio of about 1.2 to about 2.0.

22. A process according to claim 19 wherein said high temperature process stream is at a temperature of greater than 100° C.

23. A process according to claim 19 wherein said high temperature process stream is produced in a carboxylic acid production process and wherein the high temperature process stream is generated from an oxidation reactor, high pressure distillation column, vapor generated by an oxidation reactor, a water removal column, vapor generated by the crude TPA crystallizer, purified TPA crystallizer described, or vapor generated by purified TPA crystallizers.

24. A process according to claim 19 wherein said high temperature process stream is produced in a terephthalic acid production process.

25. A process to recover thermal energy from a high temperature process stream, said process comprising:
   (a) recovering thermal energy from at least a portion of said high temperature process stream in a first heat transfer zone to produce a low pressure steam;
   (b) compressing said low pressure steam in a compression zone to produce an intermediate pressure steam; wherein said compression zone comprises a compressor; wherein said intermediate pressure steam has a pressure in the range from about 50 psig to about 260 psig;
   (c) removing at least a portion of superheat resulting from compression from said intermediate pressure steam;
   (d) recovering thermal energy from at least a portion of said intermediate pressure steam in a second heat transfer zone to produce steam condensate; and
   (e) optionally, recycling at least a portion of said steam condensate to said heat transfer zone.

26. A process according to claim 25 wherein said low pressure steam has a pressure from about 0 psig to about 40 psig.

27. A process according to claim 25, or 26 wherein said compression zone comprises at least one compression device selected from the group consisting of a centrifugal compressor, and a positive displacement compressor.

28. A process according to claim 27 wherein said high temperature process stream is at a temperature of greater than 100° C.

29. A process according to claim 25 wherein said high temperature process stream is produced in a carboxylic acid production process and wherein the high temperature process stream is generated from an oxidation reactor, high pressure distillation column, vapor generated by an oxidation reactor, a water removal column, vapor generated by the crude TPA crystallizer, purified TPA crystallizer described, or vapor generated by purified TPA crystallizers.

30. A process according to claim 25 wherein said high temperature process stream is produced in a terephthalic acid production process.

31. A process to recover thermal energy from a high temperature process stream, said process comprising:

(a) oxidizing an aromatic feedstock with a reaction mixture in a reaction zone to form an aromatic carboxylic acid-rich stream and a gaseous mixture;
(b) removing in a separation zone a substantial portion of a solvent from said gaseous mixture to form said high temperature process stream and a solvent rich stream;
(c) recovering thermal energy from at least a portion of said high temperature process stream in a first heat transfer zone to produce a low pressure steam;
(d) compressing said low pressure steam in a compression zone to produce an intermediate pressure steam; wherein said intermediate pressure steam has a pressure in the range from about 50 psig to about 260 psig; and
(e) recovering thermal energy from at least a portion of said intermediate pressure steam in a second heat transfer zone to produce steam condensate;
(f) optionally recycling at least a portion of said steam condensate to said heat transfer zone.

32. A process according to claim 31 wherein said low pressure steam has a pressure from about 0 psig to about 40 psig.

33. A process according to claim 31, or 32 wherein said compression zone comprises at least one compression device selected from the group consisting of a centrifugal compressor, a positive displacement compressor, and a steam ejector.

34. A process according to claim 33 wherein said intermediate pressure steam is superheated and wherein at least a portion of the superheat is removed from said intermediate pressure steam.

35. A process according to claim 31, or 32 wherein said compression zone comprises at least one steam ejector.

36. A process according to claim 34 wherein said steam ejector has a compression ratio of about 1.2 to about 2.0.

37. A process according to claim 35 wherein said high temperature process stream is at a temperature of greater than 100° C.

38. A process according to claim 31 wherein said high temperature process stream is produced in a carboxylic acid production process and wherein the high temperature process stream is generated from an oxidation reactor, high pressure distillation column, vapor generated by an oxidation reactor, a water removal column, vapor generated by the crude TPA crystallizer, purified TPA crystallizer described, or vapor generated by purified TPA crystallizers.

39. A process according to claim 31 wherein said high temperature process stream is produced in a terephthalic acid production process.

* * * * *

UNITED STATES PATENT AND TRADEMARK OFFICE
CERTIFICATE OF CORRECTION

| | |
|---|---|
| PATENT NO. | : 7,213,540 B2 |
| APPLICATION NO. | : 10/772819 |
| DATED | : May 8, 2007 |
| INVENTOR(S) | : Lin et al. |

It is certified that error appears in the above-identified patent and that said Letters Patent is hereby corrected as shown below:

Column 9, Line 18, Claim 10(b) "nressure" should read --pressure--.

Signed and Sealed this

Third Day of July, 2007

JON W. DUDAS
*Director of the United States Patent and Trademark Office*